United States Patent [19]

Caris et al.

[11] Patent Number: 5,047,327
[45] Date of Patent: Sep. 10, 1991

[54] TIME-STABLE LIQUID CHOLESTEROL ASSAY COMPOSITIONS

[75] Inventors: Karen R. Caris, Camarillo, Calif.; Ivan E. Modrovich, 1043 Mesa Dr., Camarillo, Calif. 93010

[73] Assignee: Ivan E. Modrovich, Camarillo, Calif.

[21] Appl. No.: 294,896

[22] Filed: Jan. 3, 1989

Related U.S. Application Data

[63] Continuation of Ser. No. 110,091, Oct. 14, 1987, abandoned, which is a continuation of Ser. No. 868,892, May 27, 1986, abandoned, which is a continuation of Ser. No. 590,220, Mar. 16, 1984, abandoned, which is a continuation of Ser. No. 364,899, Apr. 2, 1982, abandoned.

[51] Int. Cl.[5] .............................. C12Q 1/60
[52] U.S. Cl. ...................... 435/11; 435/19; 435/28
[58] Field of Search ........................... 435/11

[56] References Cited

U.S. PATENT DOCUMENTS

| | | | |
|---|---|---|---|
| 3,876,375 | 4/1975 | Maurukas | 252/408 |
| 3,884,764 | 5/1975 | Goodhue et al. | 435/11 |
| 3,907,642 | 9/1975 | Richmond | 435/11 |
| 4,045,296 | 8/1977 | Sternberg | 435/11 |
| 4,116,773 | 9/1978 | Polito | 435/11 |
| 4,143,080 | 3/1979 | Harders et al. | 435/11 |
| 4,161,425 | 7/1979 | Perry | 435/11 |
| 4,186,251 | 1/1980 | Tarbutton | 435/11 |
| 4,212,938 | 7/1980 | Gruber et al. | 435/11 |
| 4,226,713 | 10/1980 | Goldberg | 435/11 |
| 4,247,631 | 1/1981 | Nix et al. | 435/11 |
| 4,366,249 | 12/1982 | Thum et al. | 435/188 |
| 4,378,429 | 3/1983 | Modrovich | 435/11 |
| 4,409,326 | 10/1983 | Modrovich | 435/11 |

FOREIGN PATENT DOCUMENTS

| | | | |
|---|---|---|---|
| 4857 | 2/1979 | European Pat. Off. | |
| 024578 | 3/1981 | European Pat. Off. | 435/11 |
| 1429525 | 3/1976 | United Kingdom | |
| 1435400 | 5/1976 | United Kingdom | 435/11 |
| 1479994 | 7/1977 | United Kingdom | |

OTHER PUBLICATIONS

Allain, C. C. et al., "Enzymatic Determination of Total Serum Cholesterol", Clinical Chem., vol. 20, No. 4, pp. 470–475 (1974).

*Primary Examiner*—Sam Rosen
*Attorney, Agent, or Firm*—Christie, Parker & Hale

[57] ABSTRACT

There is provided a stable cholesterol assay composition which comprises an aqueous solution of at least one bile acid or salt thereof being present in an amount of up to about 5 mM; a nonionic surfactant present in an amount of from about 0.15 to about 1.5 percent volume by volume; a buffer in a concentration of from 0 to about 65 mM; and cholesterol oxidase in a concentration of at least about 0.1 kIU/l. Solution pH is from about 5.5 to about 8.5. Addition of cholesterol esterase, phenol, peroxidase and 4-aminoantipyrine provides a total cholesterol chromogen system.

16 Claims, No Drawings

TIME-STABLE LIQUID CHOLESTEROL ASSAY COMPOSITIONS

This application is a continuation of U.S. application Ser. No. 07/110,091 filed Oct. 14, 1987 abandoned, which was a continuation of U.S. application Ser. No. 06/868,892 filed May 27, 1986 abandoned, which was a continuation of U.S. application Ser. No. 06/590,220 filed Mar. 16, 1984 abandoned, which was a continuation of U.S. application Ser. No. 06/364,899 filed Apr. 2, 1982 now abandoned.

BACKGROUND OF THE INVENTION

It has been known to determine cholesterol in sera by the use of assay compositions based on cholesterol oxidase, presently from a microbial source. The reaction involved is:

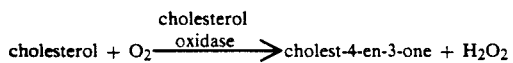

$$\text{cholesterol} + O_2 \xrightarrow{\text{cholesterol oxidase}} \text{cholest-4-en-3-one} + H_2O_2 \quad (1)$$

For total cholesterol determination, bound cholesterol may be released by the inclusion of cholesterol esterase which yields cholesterol by the reaction:

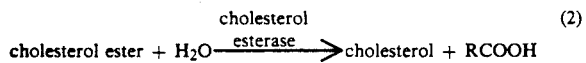

$$\text{cholesterol ester} + H_2O \xrightarrow{\text{cholesterol esterase}} \text{cholesterol} + RCOOH \quad (2)$$

The amount of cholesterol can be assayed by measuring the amount of oxygen consumed, the amount of cholest-4-en3-one formed, or the amount of hydrogen peroxide formed. A preferred way is to determine the amount of hydrogen peroxide formed by use of a chromogen system. A preferred chromogen system is one based on the presence of peroxidase from a horseradish source, phenol and antipyrine involving the reaction:

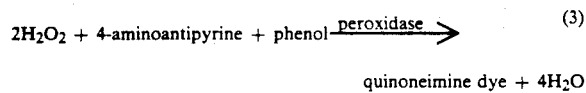

$$2H_2O_2 + \text{4-aminoantipyrine} + \text{phenol} \xrightarrow{\text{peroxidase}} \quad (3)$$

$$\text{quinoneimine dye} + 4H_2O$$

While most assay systems based on cholesterol oxidase can be made functional as prepared, they are prone to rapid degradation. As a consequence, the art early on lyophilized (freeze-dried) the composition for reconstitution at the time of use. Lyophilization is expensive and suffers from inaccuracy.

A need was recognized to provide a liquid assay system of controlled composition which would have an adequate shelf life for marketing purposes. As invented and described by one of us, and disclosed in EPC Application 80.104.568.3, filed 1 August, 1980, incorporated herein by reference, it was found that the presence of a material quantity, e.g., up to 50 percent by volume, of a polyhydroxy compound such as glycerol would induce long shelf life to a liquid assay composition. The invention enabled precise quality control to be exercised over the composition of the system, and enabled total reliability of the assay system as a tool. The system was formulated as a concentrate. Shelf life of the concentrate was more than adequate for industrial use and provided levels of stability theretofore unknown in the art.

The polyhydroxy compound, while functional to stabilize the system against degradation, increases costs and, unless proper housekeeping procedures are followed, contaminates apparatus, affecting other tests, particularly triglyceride analysis.

A desire has existed, therefore, for a liquid assay system which did not yield in performance, which could be sold as a single formulation for use as is without dilution and yet have an adequate shelf life to satisfy marketing requirements.

SUMMARY OF THE INVENTION

It has now been found that utilizing basic constituents normally present in a cholesterol assay system, but exercising exacting control over concentration of bile acid or salts thereof, nonionic surfactant and buffer, as well as pH, one can formulate a stable cholesterol assay composition which does not require a polyhydroxy compound and yet exhibits projected shelf lives of 18 months or more at 4° C., and when used with a chromogen system, rapid completion times.

The base solution employed is an aqueous solution of at least one acidic compound which is a bile acid or salt thereof, present in a concentration of up to about 5 mM, preferably from about 0.2 to about 5 mM; a nonionic surfactant, preferably propylene glycol p-isooctylphenyl ether, present in a concentration of from about 0.15 to about 1.5 percent volume by volume, preferably from about 0.2 to about 0.6 percent volume by volume; from 0 to 65 mM of a buffer, preferably from 0.5 to 50 mM, and more preferably from 0.5 to 30 mM, the preferred buffer being potassium dihydrogen phosphate ($KH_2PO_4$); and cholesterol oxidase in a concentration of at least 0.02 KIU/l, preferably at least 0.05 KIU/l, the solution having a pH of from about 5.5 to about 8.5, preferably from 6 to about 7.5.

Where it is desired to assay for total cholesterol, there is included in the composition a microbial cholesterol esterase present in a concentration of at least 0.07 KIU/l, preferably at least about 0.1 KIU/l.

The preferred composition is one containing a chromogen system for determination of hydrogen peroxide The chromogen system preferably comprises phenol in a concentration of from 8 to about 35 mM; 4-aminoantipyrine in a and peroxidase in a concentration sufficient to enable completion of a chromogen reaction, i.e., development of the pink quinoneimine dye to an intensity quantitative to hydrogen peroxide formed. For commercial practicality, they are provided in quantities sufficient to enable completion of the reaction within 10 minutes at 37° C. Preferably, the peroxidase is provided in a concentration of at least 30 KIU/l, and 4-aminoantipyrine to a concentration of about 0.3 mM.

There is preferably included in the composition a bacteriocide, with the preferred bacteriocide being 2,4 dichlorophenol, present in a concentration of up to about 1 mM, preferably from about 0.4 to about 0.6 mM.

The compositions prepared in accordance with the instant invention are stable for at least 3 days at 41° C., which is equivalent to a projected shelf life of 18 months at 4° C. or about 6 months at ambient temperature (25° C.).

When a chromogen system is employed, completion of reaction preferably occurs within 10 minutes or less at 37° C., with a color stability of at least an additional 30 minutes.

The products are prepared by first forming an aqueous solution to which there is provided buffer, bile acid or salts thereof, and surfactant. Phenol, dichlorophenol and 4-aminoantipyrine are added as required. This base composition is adjusted, if required, to an acceptable pH range by addition of a suitable acid or base.

There is separately formed an aqueous solution containing the nonionic surfactant and the enzymes which are added. The base solution and the solution of the enzymes are then combined to form a net solution.

DETAILED DESCRIPTION

According to the present invention there is provided an assay solution for the determination of cholesterol in the liquids, including sera, and which display a protracted shelf life, i.e., a shelf life of about 18 months or more at 4° C. (refrigeration conditions). Long shelf life is primarily the result of control over concentration of buffer employed.

A stable cholesterol assay composition of the instant invention comprises an aqueous solution of at least one acidic compound which is a bile acid and/or a salt of a bile acid, the total of said acidic compound being present in an amount of up to about 5mM, preferably from about 0.2 to about 5 mM; a nonionic surfactant present in a concentration of from about 0.15 to about 1.5 percent volume by volume, preferably from about 0.2 to about 0.6 percent volume by volume; a buffer in a concentration of from 0 to about 65 mM, preferably from about 0.5 to about 50 mM; cholesterol oxidase in a concentration of at least about 0.02 KIU/l, preferably at least 0.05 KIU/l, the solution having a pH of from about 5.5 to about 8.5.

For total cholesterol assay there is included microbial cholesterol esterase present in a concentration of at least about 0.07 KIU/l, preferably at least about 0.1 KIU/l.

The preferred cholesterol assay composition includes a chromogen system for determination of hydrogen peroxide.

More particularly, the preferred chromogen cholesterol assay solutions of the instant invention provide, on a perliter basis, phenol in a concentration of from about 8 to about 35 mM, preferably from about 15 to about 20 mM; bile acid and/or a salt of bile in a total amount up to about 5.0 mM, preferably from about 0.2 to about 5 mM; a nonionic surfactant, preferably polyethylene glycol p-isooctylphenyl ether (TRITON X-100), in a concentration of from about 0.15 to about 1.5 percent by volume, preferably from 0.2 to about 0.6 percent volume by volume; a buffer in a concentration of from 0 to 65 mM, preferably from about 0.5 to about 50 mM; cholesterol oxidase in a concentration of at least 0.02 KIU/l; peroxidase, preferably in a concentration of at least about 30 KIU/l; and, if present, cholesterol esterase in a concentration of at least 0.07 KIU/l, preferably at least about 0.1 KIU/l. Peroxidase and 4-aminoantipyrine are provided in an amount sufficient to enable quantitative colormetric determination of the amount of hydrogen peroxide formed from oxidation of cholesterol. It is preferred that this occur within a 10-minute completion time at 37° C. To this end, it is preferred that 4-aminoantipyrine be present in a concentration of about 0.3 mM. An acceptable range is from about 0.2 mM to about 0.35 mM. If too much or too little 4-aminoantipyrine is present, the reaction will not achieve completion, if at all, in the desired time span.

It is preferred to include in the system a bacteriocide. The preferred bacteriocide is dichlorophenol, and may be provided in a concentration of up to 0.75 mM, preferably from about 0.4 to about 0.5 mM.

The buffer is provided as required, and can be inorganic or organic in nature. Phosphates are preferred. The presently preferred buffer is potassium dihydrogen phosphate ($KH_2OP_4$).

The preferred acidic compound is cholic acid or a metal salt thereof. The presently preferred compound is sodium cholate.

The chromogen cholesterol assay compositions of the instant invention display the ability to recover, i.e., detect, cholesterol; and preferably provide an assay completion time within 10 minutes at 37° C. to a pink color, the developed intensity of which is stable for at least 30 additional minutes. The compositions have a projected stability of at least 18 months at 4° C., or a shelf life of about 6 months at room temperature, as determined by a requirement that they are stable for at least 3 days at 41° C. The chromogen assay systems of the invention are used as such and do not require dilution.

In the chromogen cholesterol assay compositions of the instant invention, a lower level of phenol concentration defines the point at which the system will lose stability, and the upper concentration defines the point at which phenol has reached a concentration where there may be an adverse effect upon color.

Besides being functional as a bacteriocide, dichlorophenol may help speed color development, and therefore is a highly desirable constituent, independent of its bacteriocide function.

The upper level of buffer concentration is critical. If the concentration is too high, completion time will be too slow, giving unreliable results and, quite unexpectedly, there will be an adverse effect on shelf life.

A bile acid or a bile salt is essential. In the absence thereof, the system fails to recover cholesterol. By contrast, at a concentration above about 5 mM, completion times are too long for commercial utility.

The nonionic surfactant has been observed to activate the enzymes, particularly cholesterol esterase. In its absence, reaction time is too long, and if present in too high a concentration will result in foaming and may have an adverse effect on viscosity.

The cholesterol oxidase used in the practice of this invention is currently of a microbial nature. The presently utilized cholesterol oxidase is that manufactured and sold by Whatman Biochemicals, Inc., of England. It has been observed that cholesterol oxidase of the Brevi bacterium is non-functional. Cholesterol esterase is from any microbial source, and that used is manufactured and sold by Kyowa Hakko Kogyo Company, Ltd., of Japan, understood to be produced from the microorganism pseudomonas fluorescens, ATCC 1126. The peroxidase used is, conveniently, horseradish peroxidase.

The products are prepared by first forming an aqueous solution to which there is provided buffer, bile acid or salts thereof, and surfactant. Phenol, dichlorophenol and 4-aminoantipyrine are added as required. This base composition is adjusted, if required, to an acceptable pH range by addition of a suitable acid or base.

There is separately formed an aqueous solution containing the nonionic surfactant and the enzymes which are added. The base solution and the solution of the enzymes are then combined to form a net solution.

The following is the presently preferred chromogen composition, based on the total volume of 1 liter:

| Component | Concentration |
| --- | --- |
| Phenol | 17 mM |
| $KH_2PO_4$ | 12.5 mM |
| 2,4 dichlorophenol | 0.49 mM |
| 4-aminoantipyrine | 0.295 mM |
| Cholic acid | 2.3 mM |
| Cholesterol oxidase | 0.05 KIU/l |
| Cholesterol esterase | 0.1 KIU/l |
| Peroxidase | 30 KIU/l |
| Triton X-100 | 0.4 ± .2 v/v |

Without limiting, the following Examples and Controls illustrate the various parameters associated with the compositions of the instant invention.

EXAMPLE 1

There was formulated a cholesterol assay system by forming a clear base solution of the following composition:

| Component | Concentration |
| --- | --- |
| Water (triple-distilled deionized) | 0.955 liter |
| Triton X-100 (10% v/v solution) | 32.0 ml |
| $KH_2PO_4$ | 12.5 mM |
| 2,4 dichlorophenol | 0.49 mM |
| 4-aminoantipyrine | 0.3 mM |
| Phenol | 17.0 mM |
| Sodium Cholate | 2.3 mM |
| pH | 7.0 |

A clear enzyme solution was formed by addition to 10 ml of an aqueous solution containing Triton X-100, sufficient cholesterol oxidase to provide cholesterol oxidase in a net solution of 0.1 KIU/l, cholesterol esterase in an amount sufficient to provide in the net solution a cholesterol esterase concentration of 0.2 KIU/l, and peroxidase in an amount sufficient to provide in the net solution peroxidase in a concentration of 30 KIU/l.

The enzyme solution was combined with the base solution. The solution recovered cholesterol in an assay with less than a 10-minute completion time at 37° C. The color formed had a stability of greater than 30 minutes, and had a lifetime of in excess of 3 days at 41° C., which is an equivalent of a shelf life of 18 months at 4° C. and about 6 months at room temperature.

Detailed studies were made of variations of the assay composition prepared according to Example 1. The parameters varied were buffer concentration, pH, cholic acid concentration and nonionic detergent concentration. For purposes of all Examples and Controls, the following meanings or codes universally apply:

1 = No change
2 $A_i'$ = Initial absorbence at 500 nm at 37° C. must be less than or equal to 0.15 for a pass
2 = A control manufactured and sold by Beckman Instruments, Inc. that is specific to cholesterol
3 = Mean or principle assigned value (PAV) to the control times 1 or the factor shown
4 = Lot number of Control
5 = A control manufactured and sold by Beckman Instruments, Inc. for multiple assay, including cholesterol
6 = A cholesterol control manufactured and sold by New England Reagent Laboratories. Cholesterol concentration was 200 mg/dl
T = TRITON X-100 = a polyethylene glycol p-isooctylphenyl ether having an average formula of $C_{34}H_{62}O_{11}$ and a formula weight of 646, manufactured and sold by Eastman Chemicals Completion times are for Beckman references at a cholesterol concentration of 600 mg/dl.

Color stability is for a cholesterol concentration of 50 mg/dl (low) and/or 500 mg/dl (high). Numerical value given is % change at the time stated.

One or more of the following constitutes failure:
a) no recovery (detection) of cholesterol;
b) greater than 10 minutes completion time at 37° C.; this is failure on the basis that longer completion times are commercially unacceptable;
c) color stability for less than 30 minutes beyond completion time; and/or
d) stability for less than three days at 41° C. (stressed).

Failure is also considered to occur if initial absorbent $A_i'$ is greater than 0.15 and cholesterol recovery (level detected) is not within ±5% of sample.

EXAMPLES 2–7 AND CONTROLS A–C

Buffer Concentration

The solution, formulated in accordance with Example 1 was modified in respect of $KH_2PO_4$ concentration. All other constituents were kept constant.

Table I compares performance as formulated (fresh) and after stressed by being heated to 41° C. for the time specified in the Table. Controls A, B and C failed because of long completion times after stress.

TABLE I

| Example or Control | Reagent Condition | pH | Color Stability Low/ High | Buffer Concentration mM/L | Completion Time Minutes | $A_i'$ | 2.5X Beckman Reference 587.5 C-011044[4] | Decision I[5] 125[3] C-007014[4] | Decision II[5] 139[3] C-104032[4] | Decision III[5] 211[3] C-007016[4] | 2X Decision III[5] 422[3] | 3X Decision III[5] 633[3] |
| --- | --- | --- | --- | --- | --- | --- | --- | --- | --- | --- | --- | --- |
| Example 2 | Fresh | ~7.0 | 0[1]/2.2% | 0.0 | 3 | .008 | — | — | — | — | — | — |
|  | 82 hrs. at 41° C. | ~7.0 |  |  | 6 | .028 | 615 | 144 | 144 | 229 | 427 | 630 |
| Example 3 | Fresh | ~7.0 | 0/4.0% | 1.0 | 3 | .008 | 604 | 133 | 146 | 225 | 452 | 647 |
|  | 82 hrs. at 41° C. | ~7.0 |  |  | 7 | .028 | 603 | 137 | 144 | 225 | 440 | 646 |
| Example 4 | Fresh | ~7.0 | 0/2.2% | 5.0 | 3 | .008 | 593 | 131 | 142 | 224 | 442 | 653 |
|  | 82 hrs. at 41° C. | ~7.0 |  |  | 7 | .031 | 599 | 133 | 145 | 220 | 442 | 654 |
| Example 5 | Fresh | ~7.0 | 0/1.5% | 12.5 | 3 | .008 | 590 | 130 | 144 | 222 | 443 | 652 |
|  | 82 hrs. at 41° C. | ~7.0 |  |  | 7 | .035 | 598 | 132 | 144 | 222 | 441 | 653 |
| Example 6 | Fresh | ~7.0 | 0/0 | 25.0 | 3 | .008 | 589 | 131 | 143 | 222 | 441 | 643 |
|  | 82 hrs. at 41° C. | ~7.0 |  |  | 8.5 | .038 | 604 | 132 | 144 | 222 | 439 | 652 |
| Example 7 | Fresh | ~7.0 | 0/0 | 50.0 | 3 | .008 | 588 | 131 | 146 | 222 | 442 | 652 |

TABLE I-continued

| Example or Control | Reagent Condition | pH | Color Stability Low/ High | Buffer Concentration mM/L | Completion Time Minutes | $A_i$ | 2.5X Beckman Reference[2] 587.5 C-011044[4] | Decision I[5] 125[3] C-007014[4] | Decision II[5] 139[3] C-104032[4] | Decision III[5] 211[3] C-007016[4] | 2X Decision III[5] 422[3] | 3X Decision III[5] 633[3] |
|---|---|---|---|---|---|---|---|---|---|---|---|---|
| | 82 hrs. at 41° C. | ~7.0 | | | 8.5 | .040 | 609 | 130 | 144 | 220 | 439 | 659 |
| Control A | Fresh | ~7.0 | —/— | 75.0 | 3 | .008 | | | | | | |
| | 82 hrs. at 41° C. | ~7.0 | | | 15 | .045 | | | | | | |
| Control B | Fresh | ~7.0 | —/— | 100.0 | 5 | .008 | | | | | | |
| | 48 hrs. at 41° C. | ~7.0 | | | 13 | .038 | | | | | | |
| Control C | Fresh | ~7.0 | —/— | 200.0 | 4-5 | .008 | | | | | | |
| | 48 hrs. at 41° C. | ~7.0 | | | 25 | .053 | | | | | | |

EXAMPLES 8, 9 AND CONTROLS D-I

Evaluation of pH

Using the assay solution prepared according to Example 1, pH was changed using HCl or NaOH to determine its effect on performance. Using the same references of Examples 2-7, the results are shown in Table II.

Failures were due to too long a completion time. Controls D, H and I failed as prepared. Controls E and F failed after stressed for 48 hours, while Control G failed after stressed after 82 hours. Color stability was after 45 minutes.

TABLE II

| Example or Control | Reagent Condition | pH | Color Stability Low/ High | Completion Time Minutes | $A_i$ | Beckman Reference[2] 2.5X C-011044[4] | Decision I[5] 125[3] C-007014[4] | Decision II[5] 139[3] C-104032[4] | Decision III[5] 211[3] C-007016[4] | 2X Decision III[5] 422[3] | 3X Decision III[5] 633[3] |
|---|---|---|---|---|---|---|---|---|---|---|---|
| Control D | Fresh | 3.5 | | 14 | .008 | | | | | | |
| Control E | Fresh | 4.0 | | 10 | .008 | | | | | | |
| | 48 hrs. at 41° C. | | | >30 | .188 | | | | | | |
| Control F | Fresh | 5.0 | | 9¾ | .008 | | | | | | |
| | 48 hrs. at 41° C. | | | FAIL | .072 | | | | | | |
| Example 8 | Fresh | 6.0 | 0/0 | 3½ | .008 | 592 | 131 | 148 | 225 | 450 | 667 |
| | 48 hrs. at 41° C. | | | 5 | .026 | | | | | | |
| | 82 hrs. at 41° C. | | | 7½ | .036 | 593 | 134 | 149 | 229 | 453 | 674 |
| Example 9 | Fresh | 7.0 | 3.5%/0 | 3 | .008 | 589 | 130 | 143 | 222 | 441 | 655 |
| | 48 hrs. at 41° C. | | | 5 | .024 | | | | | | |
| | 82 hrs. at 41° C. | | | 6½-7 | .032 | 594 | 127 | 145 | 226 | | 661 |
| Control G | Fresh | 8.0 | | 5¾ | .008 | | | | | | |
| | 48 hrs. at 41° C. | | | 7 | .046 | | | | | | |
| | 82 hrs. at 41° C. | | | 11 | .065 | | | | | | |
| Control H | Fresh | 9.0 | | >16 | .008 | | | | | | |
| Control I | Fresh | 9.5 | | >15 | .008 | | | | | | |

EXAMPLES 10-14 AND CONTROLS J, K

Cholic Acid Effect

Using the assay composition of Example 1, cholic acid concentration was varied, with all other factors kept constant. The results are shown in Table III. Control J failed because the system was turbid, and collapsed when applied to human sera. Control K failed because completion time in human sera was too long, even on stress of the solution by heating to 41° C. for 72 hours. Color stability was after 75 minutes at 37° C.

TABLE III

| Example or Control | Cholic Acid g/l | Cond. | pH | Color Stability Low/ High | Completion Time Minutes | Completion Time Sera Minutes | $A_i$ | NERL[6] 200 mg/dl | Decision I[5] 124[3] C-007014[4] | Decision II[5] 134[3] C-104032[4] | Decision III[5] 211[3] C-007016[4] | 2X Decision III[5] 422[3] | 3X Decision III[5] 633[3] |
|---|---|---|---|---|---|---|---|---|---|---|---|---|---|
| Control J | 0.0 | Fresh | 7.0 | | | ~5-6 | | 200 | | | | | |
| | | 72 hrs. at 41° C. | 7.0 | 0/<1% | (Turbidity) COLLAPSE | 6,6 | .045 | | 114 | 127 | 192 | 278 | 559 |

TABLE III-continued

| Example or Control | Cholic Acid g/l | Cond. | pH | Color Stability Low/ High | Completion Time Sera Minutes | Completion Time Minutes | $A_i$ | NERL[6] 200 mg/dl | Decision I[5] 124[3] C-007014[4] | Decision II[5] 134[3] C-104032[4] | Decision III[5] 211[3] C-007016[4] | 2X Decision III[5] 422[3] | 3X Decision III[5] 633[3] |
|---|---|---|---|---|---|---|---|---|---|---|---|---|---|
| Example 10 | 0.1 | Fresh | 7.0 | | | | | | | | | | |
| | | 72 hrs. at 41° C. | 7.0 | | 7 | 7 | .037 | | | | | | |
| Example 11 | 0.3 | Fresh | 7.0 | | | | | | | | | | |
| | | 72 hrs. at 41° C. | 7.0 | | 6½ | 6 | .033 | | | | | | |
| Example 12 | 0.75 | Fresh | 7.0 | | | | | | | | | | |
| | | 72 hrs. at 41° C. | 7.0 | | 6 | 6 | .032 | | | | | | |
| Example 13 | 1.0 | Fresh | 7.0 | | | ~5–6 | | | | | | | |
| | | 72 hrs. at 41° C. | 7.0 | 0/<2% | 5 | 7 | .034 | | | 122 | 135 | | |
| Example 14 | 1.5 | Fresh | 7.0 | | | | | | | | | | |
| | | 72 hrs. at 41° C. | 7.0 | | 5¾ | 7 | .035 | | | | | | |
| Control K | 2.0 | Fresh | 7.0 | | | ~6–7 | | | | | | | |
| | | 72 hrs. at 41° C. | 7.0 | /<1% | 10½ | 8½ | .036 | | | 123 | 138 | 209 | 411 | 614 |

EXAMPLES 15–20 AND CONTROLS L, M

Nonionic Surfactant

Since the enzymes require some nonionic surfactant in (Triton X-100) for initial enzyme stability, "0" in Control L of Table IV means a concentration on a volume basis of 6 parts per 10,000 parts. Completion times for non-sera were at a cholesterol concentration of 567.5 mg/dl. Cholesterol concentration of the sera used for sera completion time was 650 mg/dl. Control L failed because of too long a completion time in sera.

Where, in the above Controls, failure is due to too long a completion time, as opposed to inability to recover cholesterol after stress, it is considered only to define a composition considered to have a commercial lack of utility, as completion time is important. Therefore, the specification of the claims is oriented to a commercial product of short completion times. It will be considered, however, to be in the invention a system having longer completion times, provided they have adequate shelf life.

What is claimed is:

TABLE IV

| Example or Control | T* | Cond. | pH | Color Stability Low/High | Completion Time Sera Minutes | Completion Time Minutes | $A_i$ | NERL 200 mg/dl SERA | Decision I[5] 123[3] C-007014[4] | Decision III[5] 211[3] C-007016[4] | 2X Decision III[5] 422[3] | 3X Decision III[5] 633[3] |
|---|---|---|---|---|---|---|---|---|---|---|---|---|
| Control L | 0.0 | Fresh | 7.02 | | | 7 | | | | | | |
| | | 72 hrs. at 41° C. | 7.01 | 2%/<1% | 20 | 9 | .031 | 263 | 124 | 209 | 408 | 603 |
| Control M | 0.11 | Fresh | 7.02 | | | 7.5 | | | | | | |
| | | 72 hrs. at 41° C. | 7.01 | 2%/<1% | | 10 | | | | | | |
| Example 15 | 0.21 | Fresh | 7.02 | | | 7 | | | | | | |
| | | 72 hrs. at 41° C. | 7.01 | 2%/<1% | | 9.5 | | | | | | |
| Example 16 | 0.29 | Fresh | 7.02 | | | 8 | | | | | | |
| | | 72 hrs. at 41° C. | 7.01 | 2%/<1% | | 9 | | | | | | |
| Example 17 | 0.38 | Fresh | | | 3.5 | 7.5 | | | | | | |
| | | 72 hrs. at 41° C. | | 0%/<1% | 5.25 | 8, 7.5 | | 250 | 122 | 206 | 407 | 616 |
| Example 18 | 0.70 | Fresh | 7.02 | | | 8 | | | | | | |
| | | 72 hrs. at 41° C. | 7.01 | 0%/<1% | 6.5 | 8, 8.25 | | 252 | 121 | 206 | 413 | 613 |
| Example 19 | 1.02 | Fresh | 7.02 | | 3.5 | 8 | | | | | | |
| | | 72 hrs. at 41° C. | 7.01 | | | | | | | | | |
| Example 20 | 1.34 | Fresh | 7.02 | | | 8 | | | | | | |
| | | 72 hrs. at 41° C. | 7.01 | /0% | | | | | | | | |

*Triton X-100 Concentration Percent Volume by Volume

1. A stable cholesterol assay composition which consists essentially of a polyhydroxy compound free aqueous solution of:
   (a) at least one acidic compound selected from the group consisting of a bile acid and a salt of a bile acid, the total of said acidic compound being present in a positive amount of up to about 5 mM;
   (b) a nonionic surfactant present in a concentration of from about 0.15 to about 1.5 percent volume by volume;
   (c) a buffer in a concentration of from 0 to about 65 mM;
   (d) cholesterol oxidase in a concentration of at least about 0.02 KIU/l,
   (e) microbial cholesterol esterase in a concentration of at least about 0.07 KIU/l; and
   (f) a chromogen system for determining of hydrogen peroxide; said cholesterol assay solution having a pH of from about 5.5 to about 8.5 a stability of at least 3 days at 41° C. and an essay completion time within 10 minutes at 37° C.

2. A stable cholesterol assay composition as claimed in claim 1 which includes 2,4 dichlorophenol in a concentration of up to about 1 mM.

3. A stable cholesterol assay composition which consists essentially of a polyhydroxy compound free aqueous solution of:
   (a) at least one acidic compound selected from the group consisting of a bile acid and a salt of a bile acid, the total of said acidic compound being present in an amount of up to about 5 mM;
   (b) a nonionic surfactant present in a concentration of from about 0.15 to about 1.5 percent volume by weight;
   (c) a buffer in a concentration of from 0 to about 65 mM;
   (d) cholesterol oxidase in a concentration of at least about 0.02 KIU/l,
   (e) microbial cholesterol esterase in a concentration of at least about 0.07 KIU/l; and
   (f) a chromogen system for determination of hydrogen peroxide; comprising phenol in a concentration of from about 8 to about 35 mM, and peroxidase and 4-aminoantipyrene in a concentration sufficient to provide a colometric quantitative determination of hydrogen peroxide formed from oxidation of cholesterol within 10 minutes at 37° C., said cholesterol assay solution having a pH of from about 5.5 to about 8.5 and a stability of at least 3 days at 41° C.

4. A stable cholesterol assay composition as claimed in claim 3 which includes a bacteriocide.

5. A stable cholesterol assay composition as claimed in claim 4 in which the bacteriocide is 2,4 dichlorophenol, present in a concentration of up to about 1 mM.

6. A stable cholesterol assay composition as claimed in claim 3 in which pH is from about 6 to about 7.5.

7. A stable cholesterol assay composition as claimed in claim 5 in which the nonionic surfactant is polyethylene glycol p-isooctylphenyl ether, present in a concentration of from about 0.2 to about 0.6 percent volume by volume.

8. A stable cholesterol assay composition as claimed in claim 7 in which the buffer is potassium dihydrogen phosphate and in which the acidic compound is a metal salt of cholic acid.

9. A stable total cholesterol chromogen assay composition consisting essentially of polyhydroxy compound free aqueous solution having a pH of from about 6.5 to about 8.5 and comprising:
   (a) phenol in a concentration of from about 8 to about 35 mM;
   (b) a metal salt of cholic acid present in a positive amount up to about 5 mM;
   (c) a nonionic surfactant present in a concentration of from about 0.2 to about 1.5 percent volume by volume;
   (d) a buffer present in a concentration of from 0 to about 65 mM;
   (e) 4-aminoantipyrine;
   (f) microbial cholesterol esterase present in a concentration of at least about 0.07 KIU/l;
   (g) cholesterol oxidase present in a concentration of at least about 0.02 KIU/l; and
   (h) peroxidase, the amount of peroxidase and 4-aminoantipyrine being sufficient to enable quantitative determination of the amount of hydrogen peroxide formed from oxidation of cholesterol within 10 minutes at 37° C., said assay composition having a stability of at least 3 days at 41° C.

10. A stable total cholesterol chromogen assay composition as claimed in claim 9 in which the buffer is potassium dihydrogen phosphate, present in a concentration of from about 0.5 to about 30 mM, and in which pH is from about 6 to about 7.5.

11. A stable total cholesterol chromogen assay composition as claimed in claim 10 in which peroxidase is present in a concentration of at least about 30 KIU/l and in which 4-aminoantipyrine is present in a concentration of about 0.3 mM and the nonionic surfactant is polyethylene glycol p-isooctylphenyl ether, present in a concentration of from about 0.2 to about 0.4 percent volume by volume.

12. A stable total cholesterol chromogen assay composition consisting essentially of a polyhydroxy compound free aqueous solution of:
   (a) phenol in a concentration of about 17 mM;
   (b) 2,4 dichlorophenol present in a concentration of about 5.5 mM;
   (c) a metal salt of cholic acid present in a positive amount up to about 5 mM;
   (d) polyethylene glycol p-isooctylphenyl ether present in a concentration of from about 0.2 to about 0.6 percent volume by volume;
   (e) $KH_2PO_4$ present in a concentration of about 12.5 mM;
   (f) peroxidase present in a concentration of about 30 KIU/l;
   (g) cholesterol oxidase present in a concentration of at least about 0.05 KIU/l;
   (h) microbial cholesterol esterase present in a concentration of at least about 0.2 KIU/l; and
   (i) 4-aminoantipyrene present in a concentration of about 0.3 mM, said stable total cholesterol chromogen assay composition having a pH of from about 6.0 to about 7.5 and a stability of at least 3 days at 41° C.

13. A stable total cholesterol assay composition as claimed in claim 12 in which the cholesterol oxidase is present in a concentration of at least about 0.1 KIU/l.

14. A stable total cholesterol assay composition as claimed in claim 12 in which the cholesterol esterase is present in a concentration of at least about 0.2 KIU/l.

15. A method of preparing a stable total cholesterol chromogen assay composition consisting essentially of a base solution and an enzyme solution each being free of a polyhydroxy compound to form a net solution which:
(a) the base solution consists essentially of a major amount of water and:
  i) a metal salt of cholic acid in an amount sufficient to be present in the net solution in a concentration of up to about 5 mM;
  ii) 2,4 dichlorophenol in an amount sufficient to be present in the net solution in a concentration of about 0.5 mM;
  iii) phenol in an amount sufficient to be present in the net solution in a concentration of about 17 mm;
  iv) $KH_2PO_4$ in an amount sufficient to be present in the net solution in a concentration of about 12.5 mM;
  v) 4-aminoantipyrine in an amount sufficient to be present in the net solution in a concentration of about 0.3 mM; and
  vi) polyethylene glycol p-isooctylphenyl ether,
(b) the enzyme solution consisting essentially of an aqueous solution of polyethylene glycol p-isooctylphenyl ether and:
  i) cholesterol oxidase present in an amount sufficient to be present in the net solution in a concentration of at least about 0.05 KIU/l.
  ii) microbial cholesterol esterase in an amount sufficient to be present in the net solution in a concentration of at least about 0.1 KIU/l; and
  iii) peroxidase in an amount sufficient to be present in the net solution in a concentration of at least about 30 KIU/l, said net solution having a pH of from about 6.0 to about 7.5 and containing polyethylene glycol p-isooctylphenyl ether present in a concentration of from about 0.2 to about 0.6 percent volume by volume, said solution being capable of completing a cholesterol assay within 10 minutes at 37° C.

16. A stable total cholesterol chromagen assay composition consisting of essentially of an aqueous solution having a pH of from about 6.5 to about 7.5 and;
(a) phenol in a concentration of from about 8 to about 35 mM;
(b) sodium cholate present in a concentration of from about 0.2 to about 5 mM;
(c) a nonionic surfactant present in a concentration of from about 0.15 to about 1.5 percent volume by volume;
(d) a buffer present in a concentration of from 0.5 to about 65 mM;
(e) 4-aminoantipyrine;
(f) microbial cholesterol esterase present in a concentration of at least about 0.07 KIU/l;
(g) cholesterol oxidase present in a concentration of at least about 0.02 KIU/l; and
(h) peroxidase, the amount of peridase and 4-aminoantipyrine being sufficient to enable quantitative determination of the amount of hydrogen peroxide formed from oxidation of cholesterol within 10 minutes at 37° C., said assay composition having a stability of at least 3 days at 41° C.

* * * * *

UNITED STATES PATENT AND TRADEMARK OFFICE
CERTIFICATE OF CORRECTION

PATENT NO. : 5,047,327
DATED : September 10, 1991
INVENTOR(S) : Karen R. Caris; Ivan E. Modrovich It is certified that error appears in the above-identified patent and that said Letters Patent is hereby corrected as shown below:

Abstract, line 8, change "kIU/l" to -- KIU/l --.

Column 1, line 33, change "en3" to -- en-3 --.

Column 2, line 41, after "peroxide" insert a period.

Column 2, line 44, before "peroxidase" delete "and".

Column 3, line 22, change "5mM" to -- 5 mM --.

Column 3, line 40, change "perliter" to -- per liter --.

Column 4, line 4, change "($KH_2OP_4$)" to -- ($KH_2PO_4$) --.

Column 5, line 43, after "lifetime" delete "of".

Column 6, line 5, change "nm" to -- nM --.

UNITED STATES PATENT AND TRADEMARK OFFICE
CERTIFICATE OF CORRECTION

PATENT NO. : 5,047,327

DATED : September 10, 1991

INVENTOR(S) : Karen R. Caris; Ivan E. Modrovich

It is certified that error appears in the above-identified patent and that said Letters Patent is hereby corrected as shown below:

Column 11, line 17, change "determining" to -- determination --.

Column 12, line 55, change "0.2" to -- 0.1 --.

Column 13, line 15, change "mm" to -- mM --.

Column 14, line 11, before "essentially" delete "of".

Signed and Sealed this

Nineteenth Day of October, 1993

Attest:

BRUCE LEHMAN

Attesting Officer

Commissioner of Patents and Trademarks